US009737532B2

(12) United States Patent
Higami et al.

(10) Patent No.: US 9,737,532 B2
(45) Date of Patent: Aug. 22, 2017

(54) METHOD OF TREATING ISCHEMIA/REPERFUSION INJURY

(75) Inventors: Yoshikazu Higami, Tokyo (JP); Naoyuki Okita, Tokyo (JP); Shingo Matsushima, Tokyo (JP)

(73) Assignee: TOKYO UNIVERSITY OF SCIENCE FOUNDATION, Tokyo (JP)

( * ) Notice: Subject to any disclaimer, the term of this patent is extended or adjusted under 35 U.S.C. 154(b) by 0 days.

(21) Appl. No.: 13/982,541

(22) PCT Filed: Jan. 27, 2012

(86) PCT No.: PCT/JP2012/052565
§ 371 (c)(1),
(2), (4) Date: Jul. 30, 2013

(87) PCT Pub. No.: WO2012/105707
PCT Pub. Date: Aug. 9, 2012

(65) Prior Publication Data
US 2013/0317042 A1  Nov. 28, 2013

Related U.S. Application Data

(60) Provisional application No. 61/437,692, filed on Jan. 31, 2011.

(51) Int. Cl.
| | |
|---|---|
| A61K 31/496 | (2006.01) |
| A61K 31/4164 | (2006.01) |
| G01N 33/50 | (2006.01) |
| C12Q 1/68 | (2006.01) |
| G01N 33/573 | (2006.01) |

(52) U.S. Cl.
CPC ........ *A61K 31/496* (2013.01); *A61K 31/4164* (2013.01); *C12Q 1/6876* (2013.01); *G01N 33/5023* (2013.01); *G01N 33/5044* (2013.01); *G01N 33/573* (2013.01)

(58) Field of Classification Search
CPC .................................................. A61K 31/496
USPC ...................................................... 514/254.06
See application file for complete search history.

(56) References Cited

U.S. PATENT DOCUMENTS

| 7,705,007 B2 | 4/2010 | Fotouhi et al. |
| 2006/0189511 A1 | 8/2006 | Koblish et al. |
| 2011/0218206 A1 | 9/2011 | Chan |
| 2012/0302628 A1* | 11/2012 | Kastan et al. ............. 514/44 R |

FOREIGN PATENT DOCUMENTS

| EP | 2 668 960 A2 | 12/2013 |
| WO | WO-03/095625 A2 | 11/2003 |

OTHER PUBLICATIONS

Flavio Moroni and Alberto Chiarugi, "Post-ischemic brain damage: targeting PARP-1 within the ischemic neurovascular units as a realistic avenue to stroke treatment," FEBS Journal 276 (2009) 36-45.*

(Continued)

*Primary Examiner* — San-Ming Hui
(74) *Attorney, Agent, or Firm* — Marshall, Gerstein & Borun LLP

(57) ABSTRACT

An agent for treating ischemia/reperfusion injury, including a therapeutically effective amount of a p53 agonist compound including a cis-imidazoline structure.

2 Claims, 16 Drawing Sheets

(56) References Cited

OTHER PUBLICATIONS

Moroni, F. and Alberto Chiarugi, "Post-ischemic brain damage: targeting PARP-1 within the ischemic neurovascular units as a realistic avenue to stroke treatment," FEBS Journal 276 (2009) 36-45.*
Louis R. Caplan, MD; Michael Hennerici, MD, "Impaired Clearance of Emboli (Washout) is an Important Link Between Hypoperfusion, Embolism, and Ischemic Stroke," Arch Neurol. 1998;55(11):1475-1482.*
Sablina, A. et al., Nat Med Dec. 2005 11(12):1306-1313.*
Zhu, Q. et al., Oncogene (2007) 26, 4199-4208.*
Dhalla, et al. Cardiovascular Research 47 (2000) 446-456.*
Cayman Chemical Company. Caylin-2 Material Safety Data Sheet. Jan. 28, 2005. 3 pages.*
W. Nagai et al. / Biochemical and Biophysical Research Communications 421 (2012) 15-19.*
Moens, A. L. et al, International Journal of Cardiology, 100 (2005) 179-180.*
Ferraris, Evolution of poly(ADP-ribose) polymerase-1 (PARP-1) inhibitors. From concept to clinic, J. Med. Chem., 53(12):4561-84 (2010).
Green et al., Cytoplasmic functions of the tumour suppressor p53, Nature, 458(7242):1127-30 (2009).
Ha et al., Poly(ADP-ribose) polymerase is a mediator of necrotic cell death by ATP depletion, Proc. Natl. Acad. Sci. USA, 96(24):13978-82 (1999).
Herceg et al., Failure of poly(ADP-ribose) polymerase cleavage by caspases leads to induction of necrosis and enhanced apoptosis, Mol. Cell Biol., 19(7):5124-33 (1999).
Kaufmann et al., Specific proteolytic cleavage of poly(ADP-ribose) polymerase: an early marker of chemotherapy-induced apoptosis, Cancer Res., 53(17):3976-85 (1993).
Komarova et al., p53 is a suppressor of inflammatory response in mice, FASEB J., 19(8):1030-32 (2005).
Kruse et al., Modes of p53 regulation, Cell, 137(4):609-622 (209).
Lazebnik et al., Cleavage of poly(ADP-ribose) polymerase by a proteinase with properties like ICE, Nature, 371(6495):346-7 (1994).
Lee et al., The multiple levels of regulation by p53 ubiquitination, Cell Death Differ., 17(1):86-92 (2010).
Leppard et al., Physical and functional interaction between DNA ligase IIIalpha and poly(ADP-Ribose) polymerase 1 in DNA single-strand break repair, Mol. Cell Biol., 23(16):5919-27 (2003).
Masutani et al., Poly(ADP-ribosyl)ation in relation to cancer and autoimmune disease, Cell Mol. Life Sci., 62(7-8):769-83 (2005).
Matsushima et al., An Mdm2 antagonist, Nutlin-3a, induces p53-dependent and proteasome-mediated poly(ADP-ribose) polymerase1 degradation in mouse fibroblasts, Biochem. Biophys. Res. Commun., 407(3):557-61 (2011).
Miwa et al., PolyADP-ribosylation and cancer, Cancer Sci., 98(10):1528-35 (2007).
Mortusewicz et al., Feedback-regulated poly(ADP-ribosyl)ation by PARP-1 is required for rapid response to DNA damage in living cells, Nucleic Acids Res., 35(22):7665-75 (2007).
Pacher et al., Role of the peroxynitrite-poly(ADP-ribose) polymerase pathway in human disease, Am. J. Pathol., 173(1):2-13 (2008).
Sablina et al., The antioxidant function of the p53 tumor suppressor, Nat. Med., 11(12):1306-13 (2005).
Shangary et al., Small-molecule inhibitors of the MDM2-p53 protein-protein interaction to reactivate p53 function: a novel approach for cancer therapy, Annu. Rev. Pharmacol. Toxicol., 49:223-41 (2009).
Shangary et al., Temporal activation of p53 by a specific MDM2 inhibitor is selectively toxic to tumors and leads to complete tumor growth inhibition, Proc. Natl. Acad. Sci. USA, 105(10):3933-38 (2008).
Vassilev et al., In vivo activation of the p53 pathway by small-molecule antagonists of MDM2, Science, 303(5659):844-8 (2004).
Yonish-Rouach et al., Wild-type p53 induces apoptosis of myeloid leukaemic cells that is inhibited by interleukin-6, Nature, 352(6333):345-7 (1991).
Search Report in European Application No. 12741481.1 dated Sep. 25, 2014.
Dey, A. et al., Nutlin-3 inhibits the NFkB Pathway in a p53 Dependent Manner: Implications in Lung Cancer Therapy, Cell Cycle, 6(17): 2178-2185.
Japanese Patent Office, Notice of Reasons for Rejection, issued for Japanese Patent Application No. 2013-534527 on Oct. 13, 2015.

* cited by examiner

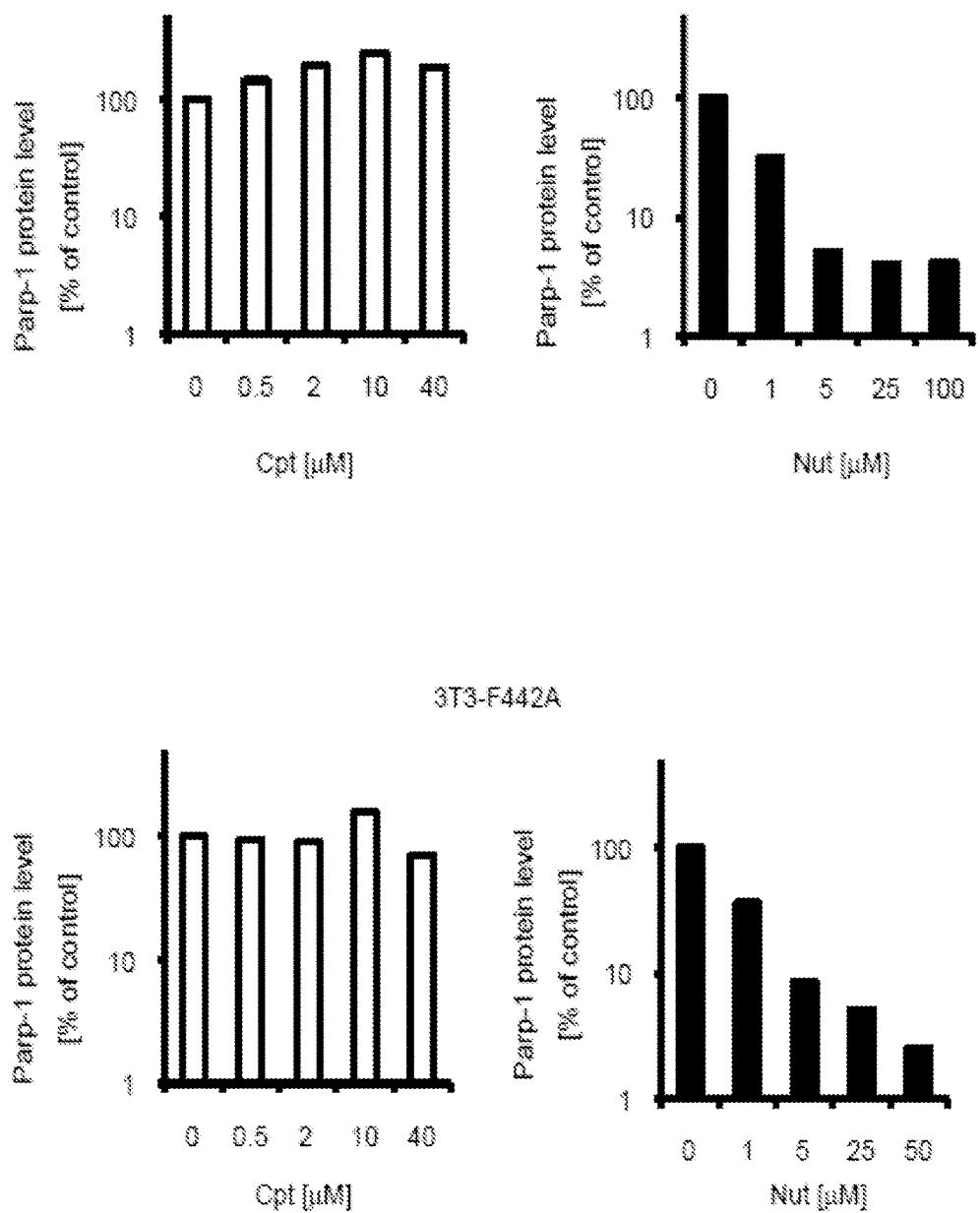

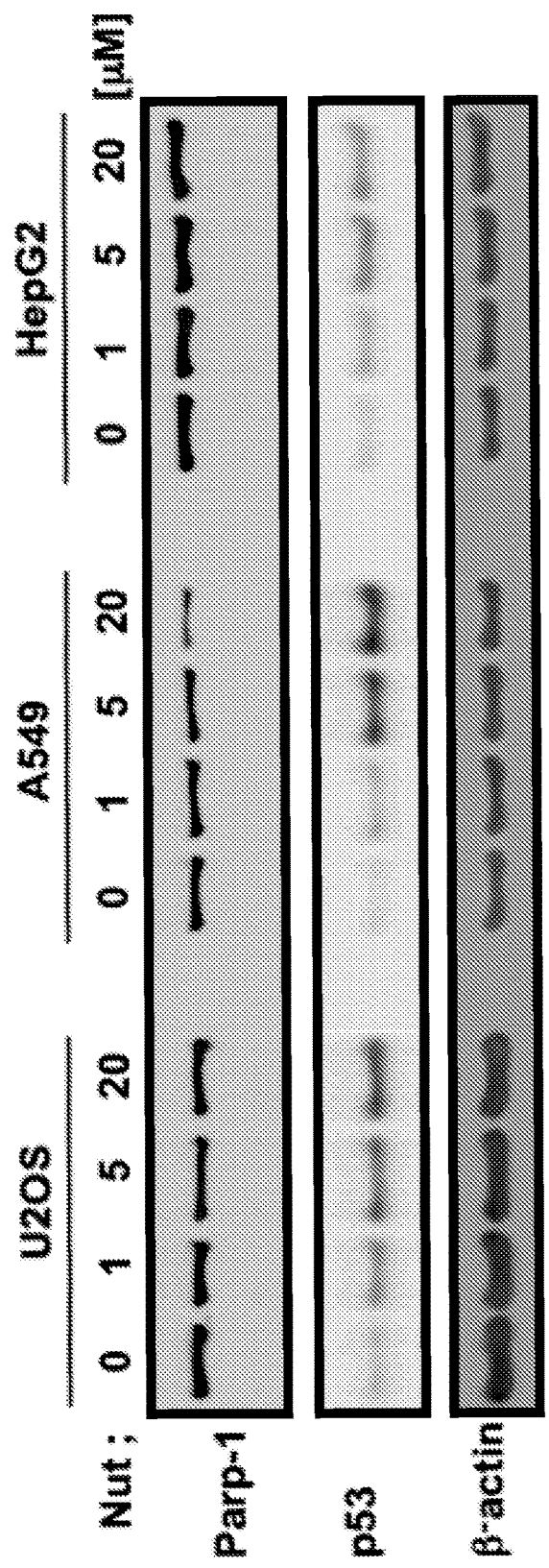

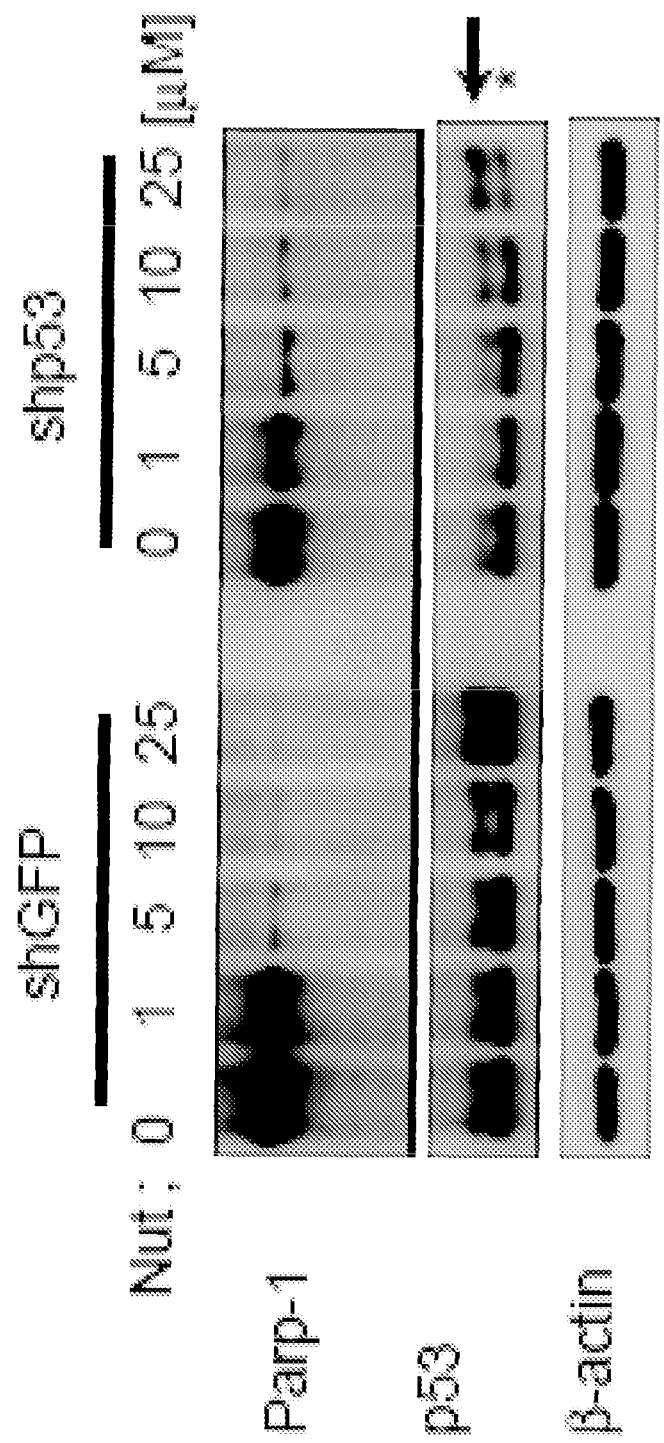

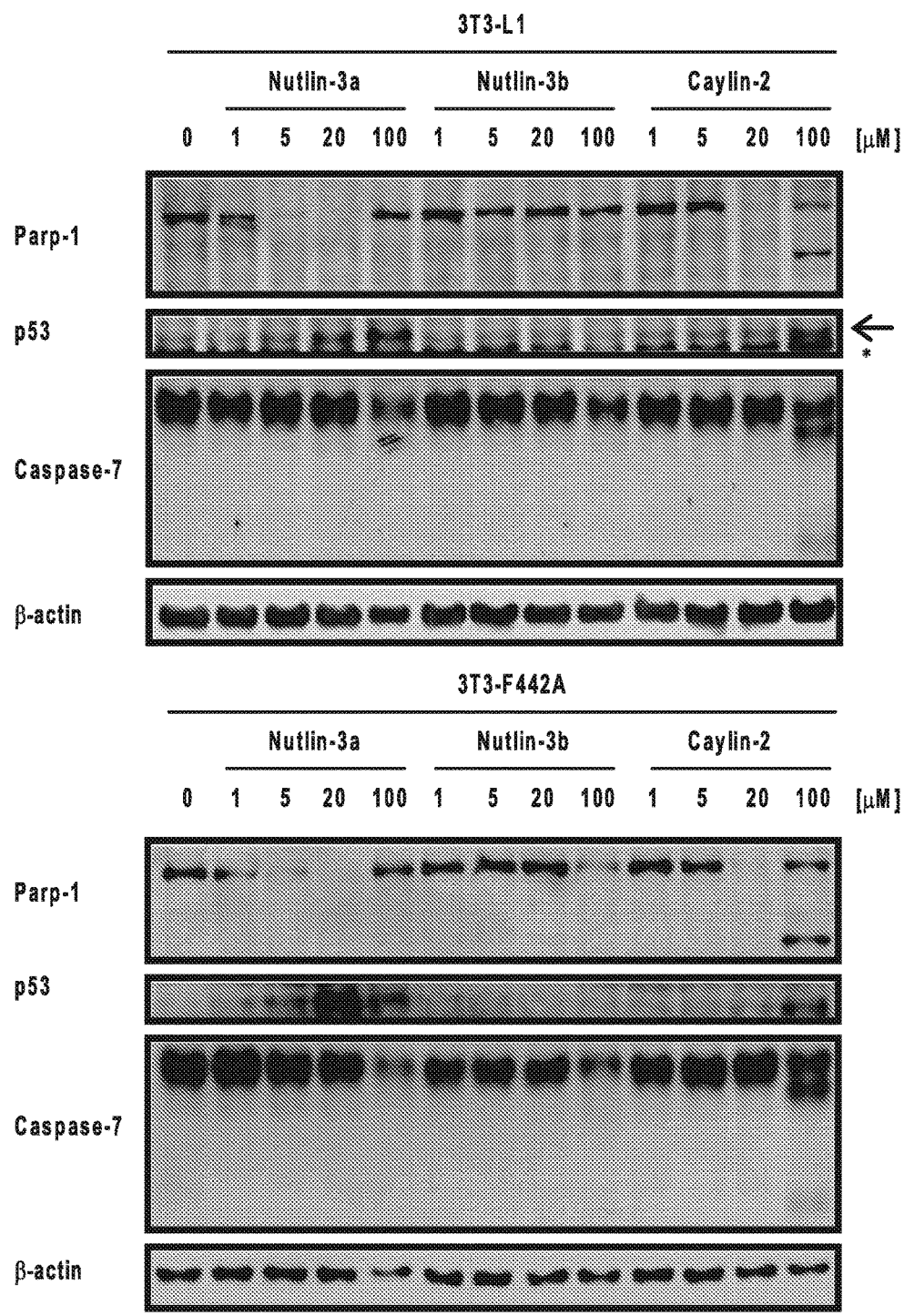

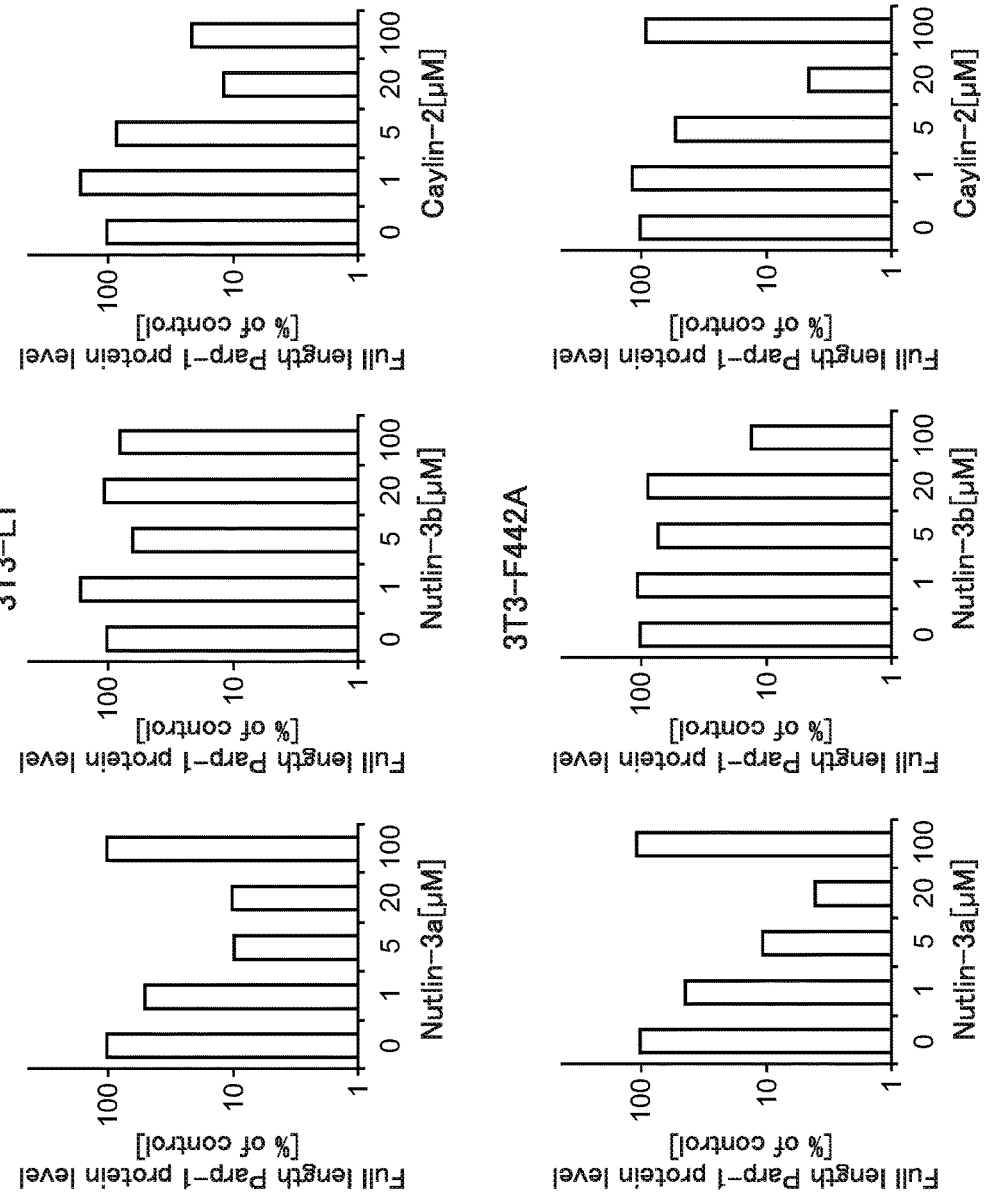

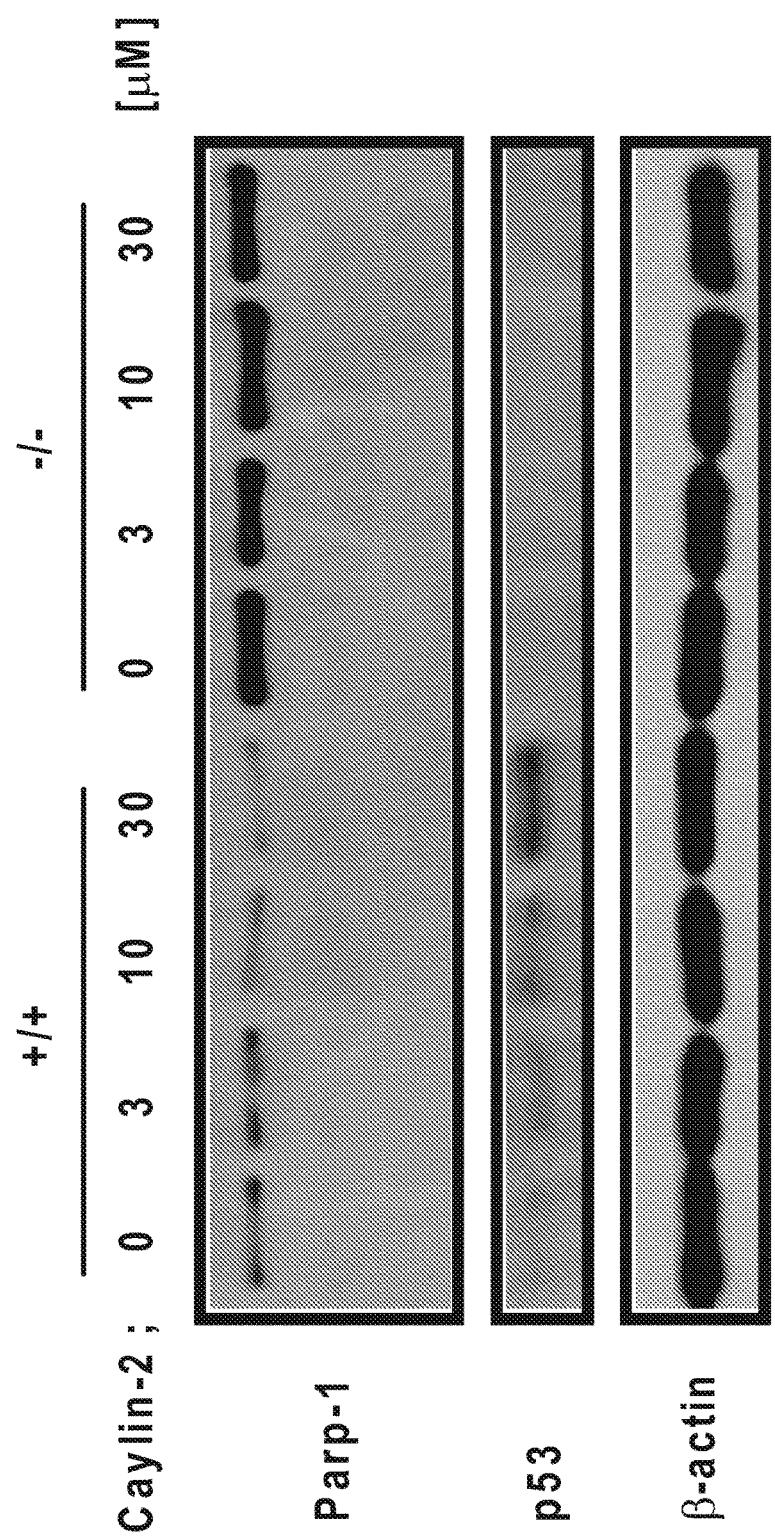

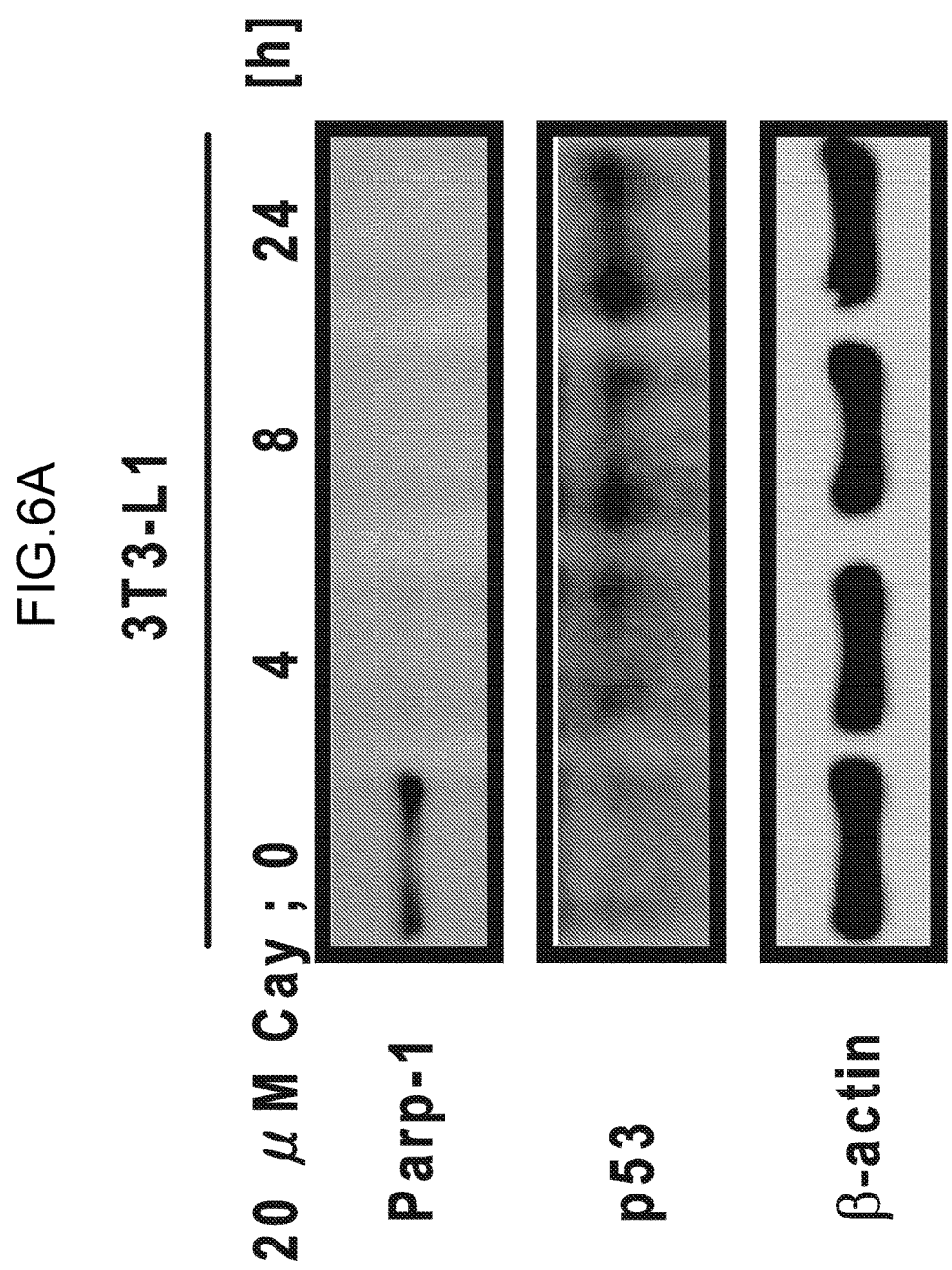

SEQUENCE LISTING

```
<160> NUMBER OF SEQ ID NOS: 9

<210> SEQ ID NO 1
<211> LENGTH: 64
<212> TYPE: DNA
<213> ORGANISM: Artificial
<220> FEATURE:
<223> OTHER INFORMATION: Synthetic polynucleotide

<400> SEQUENCE: 1
gatccccgta cgtgtgtagt agcttcttca agagaggagc tattacacat gtacttttg      60 gaaa                                                                  64

<210> SEQ ID NO 2
<211> LENGTH: 64
<212> TYPE: DNA
<213> ORGANISM: Artificial
<220> FEATURE:
<223> OTHER INFORMATION: Synthetic polynucleotide

<400> SEQUENCE: 2
agcttttcca aaagtacat gtgtaatagc tcctctcttg aagaagctac tacacacgta      60
cggg                                                                  64

<210> SEQ ID NO 3
<211> LENGTH: 29
<212> TYPE: DNA
<213> ORGANISM: Artificial
<220> FEATURE:
<223> OTHER INFORMATION: Synthetic polynucleotide

<400> SEQUENCE: 3
aattgacaag ttatgcatcc aacagtaca                                       29
```

<210> SEQ ID NO 4
<211> LENGTH: 30
<212> TYPE: DNA
<213> ORGANISM: Artificial
<220> FEATURE:
<223> OTHER INFORMATION: Synthetic polynucleotide

<400> SEQUENCE: 4
actcctcaac atcctggggc agcaacagat					30

<210> SEQ ID NO 5
<211> LENGTH: 30
<212> TYPE: DNA
<213> ORGANISM: Artificial
<220> FEATURE:
<223> OTHER INFORMATION: Synthetic polynucleotide

<400> SEQUENCE: 5
gaacctgcgt gcaatccatc ttgttcaatg					30

<210> SEQ ID NO 6
<211> LENGTH: 20
<212> TYPE: DNA
<213> ORGANISM: Artificial
<220> FEATURE:
<223> OTHER INFORMATION: Synthetic polynucleotide

<400> SEQUENCE: 6
tgctcatctt caaccagcag						20

<210> SEQ ID NO 7
<211> LENGTH: 21
<212> TYPE: DNA
<213> ORGANISM: Artificial
<220> FEATURE:
<223> OTHER INFORMATION: Synthetic polynucleotide

<400> SEQUENCE: 7
tcctttggag ttacccattc c						21

<210> SEQ ID NO 8
<211> LENGTH: 20
<212> TYPE: DNA
<213> ORGANISM: Artificial
<220> FEATURE:
<223> OTHER INFORMATION: Synthetic polynucleotide

<400> SEQUENCE: 8
tctttgcagc tccttcgttg						20

<210> SEQ ID NO 9
<211> LENGTH: 19
<212> TYPE: DNA
<213> ORGANISM: Artificial
<220> FEATURE:
<223> OTHER INFORMATION: Synthetic polynucleotide

<400> SEQUENCE: 9
ggcctcgtca cccacatag						19

METHOD OF TREATING ISCHEMIA/REPERFUSION INJURY

TECHNICAL FIELD

The invention relates to a method of treating ischemia/reperfusion injury.

BACKGROUND ART

Nutlin3a is an Mdm2 inhibitor and is potent to stabilize p53, which is a tumor-suppressor involved in various biological processes such as cell cycle regulation, DNA repair, and apoptosis (see, for example, U.S. Pat. No. 7,705,007 and Science (2004) 303, 844-848).

Caylin2 is a Nutlin-3 analog in which trifluoromethyl groups have been substituted for chlorine on the 2 phenyl rings.

p53 is a tumor-suppressor that is mutated or deleted in more than half of all human tumors. The physiological roles of p53 are versatile, forming a cell cycle checkpoint and functioning in DNA repair, apoptosis, and energy metabolism (Nature (2009) 458:1127-1130). It has been shown that phosphorylations at multiple sites and subsequent proteasomal degradation are important in the regulation of p53 protein levels (Cell (2009) 137; 609-622). p53 ubiquitination required in its degradation is catalyzed by several ubiquitin ligases such as Mdm2, Pirh2, and Cop1 (Cell Death Differ. (2010) 17; 86-92). In particular, the mechanism of regulation of p53 by Mdm2 has been well-analyzed. Because the massive stabilization of p53 was able to induce apoptosis in p53 proficient tumor cells (Nature (1991) 352; 345-347), stabilization of p53 via an inhibition of Mdm2 is one of the attractive strategies for cancer therapy. Recently, it has been reported that small molecular compounds such as Nutlin3a and MI-219 act as cell-permeable Mdm2 antagonists (Science (2004) 303; 844-848, Proc. Natl. Acad. Sci. U.S.A. (2008) 105; 3933-3938), and their analogs have progressed to preclinical development or early phase clinical trials for anti-cancer therapy (Annu. Rev. Pharmacol. Toxicol. (2009) 49; 223-241). Because p53 upregulates anti-oxidant and anti-inflammatory genes (Nat. Med. (2005) 11; 1306-1313, FASEB J (2005) 19; 1030-1032), p53 has a potential to protect from I/R-induced cellular injuries via anti-oxidative and anti-inflammatory responses.

Parp1 is a major enzyme catalyzing poly (ADP-ribosyl)ation, which is a post-translational protein modification. It is involved in replication, DNA repair, and cell death (Cell Mol. Life Sci. (2005) 62, 769-783, Cancer Sci. (2007) 98, 1528-1535). Parp1 is dramatically activated by DNA breaks and then catalyzes poly(ADP-ribosyl)ation on substrate proteins in DNA damage regions, which is required for efficient recruitment of DNA repair factors to the loci (Cell. Biol. (2003) 23, 5919-5927, Nucleic Acids Res. (2007) 35, 7665-7675). On the other hand, over-activation of Parp1 decreases cellular NAD+ and ATP levels, resulting in necrotic cell death caused by breakdown of energy metabolism (Proc. Natl. Acad. Sci. U.S.A. (1999) 96, 13978-13982, Mol. Cell. Biol. (1999) 19, 5124-5133). The involvement of Parp1 in inflammatory responses has also been reported. Ischemia/reperfusion-induced Parp1 over-activation is mediated by production of reactive oxygen species and is involved in NF-kB transactivation (Am. J. Pathol. (2008) 173, 2-13). Furthermore, Parp1 has been also characterized as a useful hallmark of apoptosis because full length Parp1 is cleaved by the apoptotic proteases, caspase-3 and -7, into p85 and p25 fragments during apoptosis (Cancer Res. (1993) 53, 3976-3985, Nature (1994) 371, 346-347). Therefore, Parp1 is an attractive target of cancer chemotherapy and protection from ischemia/reperfusion injury, and several Parp1 inhibitors are being evaluated in clinical trials (J. Med. Chem. (2010) 53, 4561-4584).

SUMMARY OF INVENTION

An object of the present invention is to provide a method of treating ischemia/reperfusion injury.

Aspects of the present invention include the following.

<1> An agent for treating ischemia/reperfusion injury, comprising a therapeutically effective amount of a p53 agonist compound comprising a cis-imidazoline structure.

<2> The agent according to <1>, wherein the p53 agonist compound comprising a cis-imidazoline structure is selected from the group consisting of Nutlin3a, Caylin2 and those pharmaceutically acceptable salts thereof.

<3> The agent according to <1> or <2>, wherein the ischemia/reperfusion injury is the tissue damage which occurs during at least one selected from the group consisting of ischemic infarction, treatment for ischemic infarction, and ischemic and reperfusion period in organ transplantation.

<4> The agent according to any one of <1> to <3>, wherein the ischemia/reperfusion injury is at least one selected from the group consisting of cerebral infarction, myocardial infarction and pulmonary infarction.

<5> A method of treating ischemia/reperfusion injury, comprising administering to a mammal a therapeutically effective amount of a p53 agonist compound comprising a cis-imidazoline structure.

<6> The method according to <5>, wherein the p53 agonist compound comprising a cis-imidazoline structure is selected from the group consisting of Nutlin3a, Caylin2 and those pharmaceutically acceptable salts thereof.

<7> The method according to <5> or <6>, wherein the ischemia/reperfusion injury is the tissue damage which occurs during at least one selected from the group consisting of ischemic infarction, treatment for ischemic infarction, and ischemic and reperfusion period in organ transplantation.

<8> The method according to any one of <5> to <7>, wherein the ischemia/reperfusion injury is at least one selected from the group consisting of cerebral infarction, myocardial infarction and pulmonary infarction.

<9> A method of screening a therapeutic agent for treating an ischemia/reperfusion injury, comprising:

contacting a test substance with a p53-wild-type tester cell, of which an expression amount of Parp1 protein in a case in which the cell is contacted with Nutlin3a or Caylin2 is lower than that before contact with Nutlin3a or Caylin2, and thereafter measuring the expression amount of Parp1 protein in the tester cell to obtain a first measurement value;

contacting the tester cell with the test substance and a proteasome inhibitor, and thereafter measuring the expression amount of Parp1 protein in the tester cell to obtain a second measurement value; and selecting the test substance as a candidate substance for use as a therapeutic agent for treating an ischemia/reperfusion injury when the second measurement value is greater than the first measurement value.

<10> The method of screening a therapeutic agent for treating an ischemia/reperfusion injury according to <9>, wherein the tester cell is a p53-wild-type mouse fetus-derived fibroblast cell.

Mouse fibroblast 3T3-L1 (upper panel) or 3T3-F442A (lower panel) cells were treated with the indicated concentrations of Cpt or Nutlin3a for 24 hours. The cell lysates were analyzed by Western blotting using the indicated antibodies. LE means long exposure.

Figure 1A:
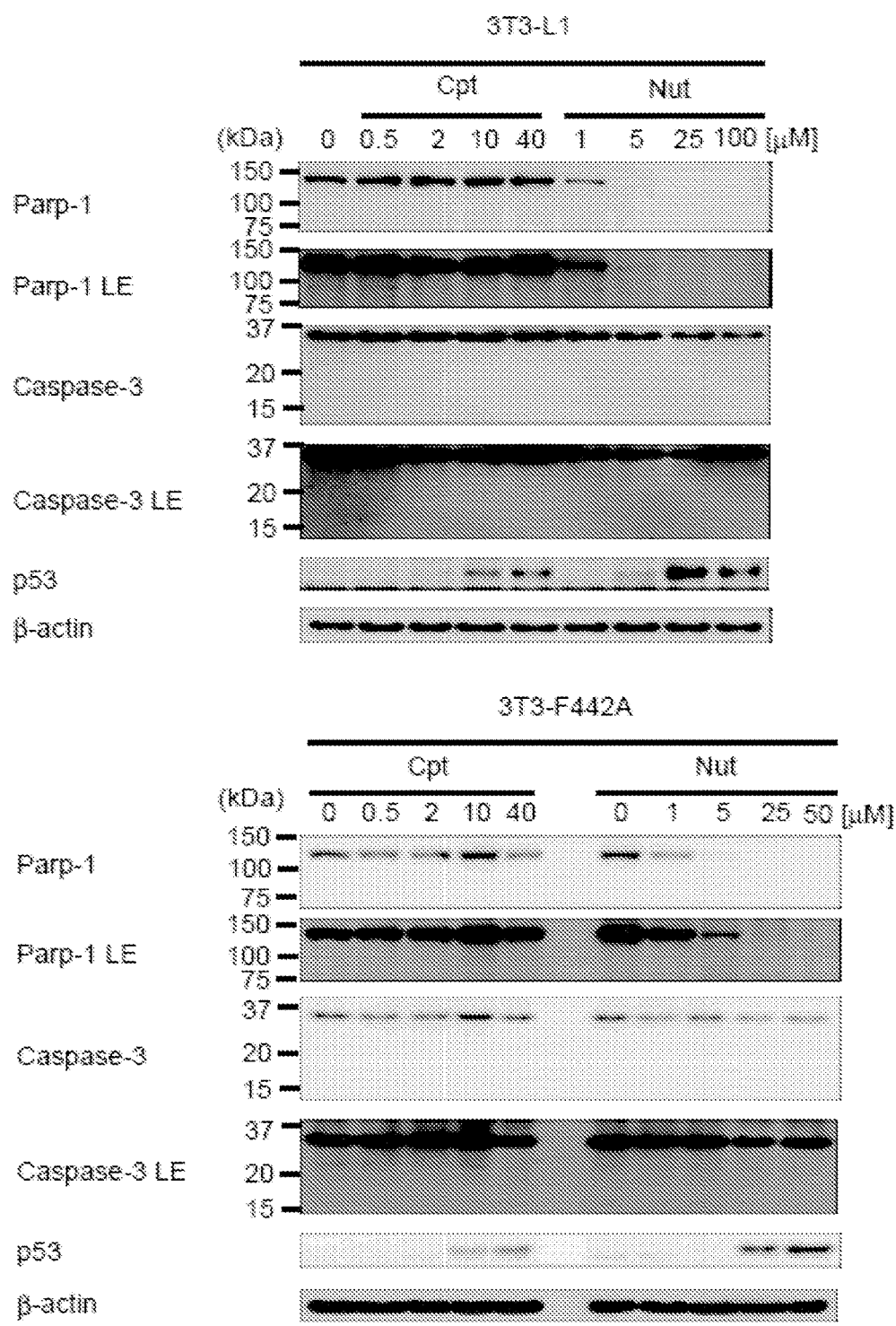
FIG. 1A shows that Nutlin3a induces a decrease in Parp1 protein levels in mammalian cell lines but that Cpt does not.

FIG. 1B is quantitative data from FIG. 1A.

Figure 1C:
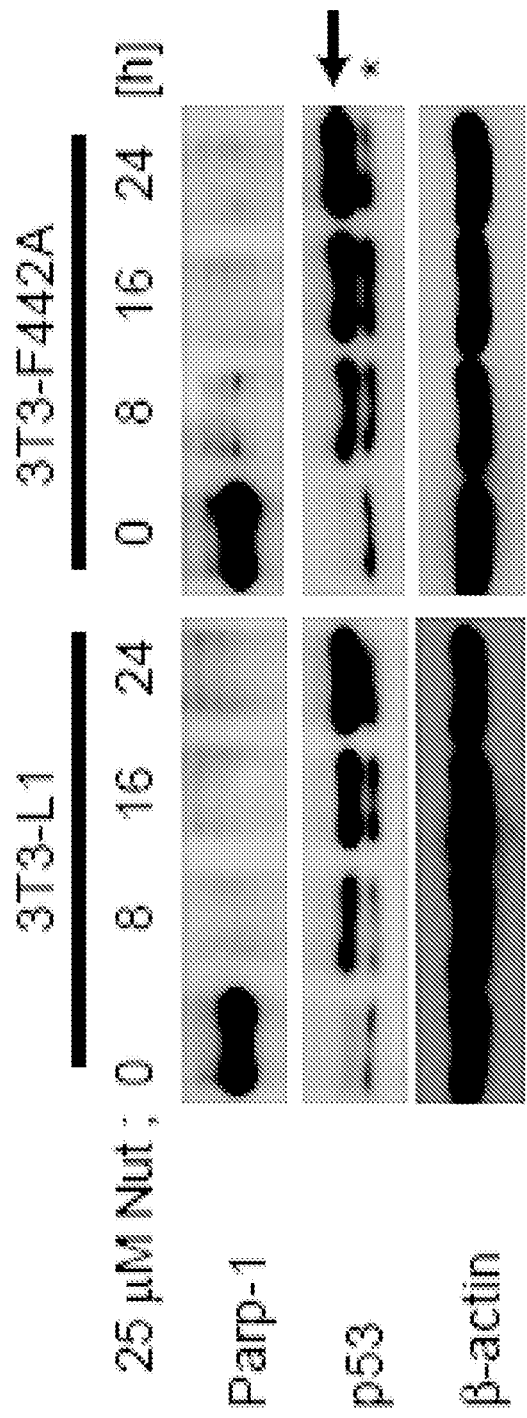

FIG. 1C shows that 3T3-L1 or 3T3-F442A cells were treated with 25 µM of Nutlin3a for the indicated times. Proteins were subjected to Western blotting. In the p53 panel, the arrow and asterisk respectively show the p53 and nonspecific bands.

FIG. 1D shows that three human cell lines (U2OS, A549, and HepG2) were treated with the indicated concentrations of or Cpt or Nutlin3a for 24 h. The cell lysates were analyzed by Western blotting using the indicated antibodies.

All experiments were performed at least three times, and representative data are shown.

FIG. 2A shows that a decrease in Parp1 protein levels induced by Nutlin3a is p53 status dependent. shGFP- and shp53-transiently transfected 3T3-L1.

Figure 2B:
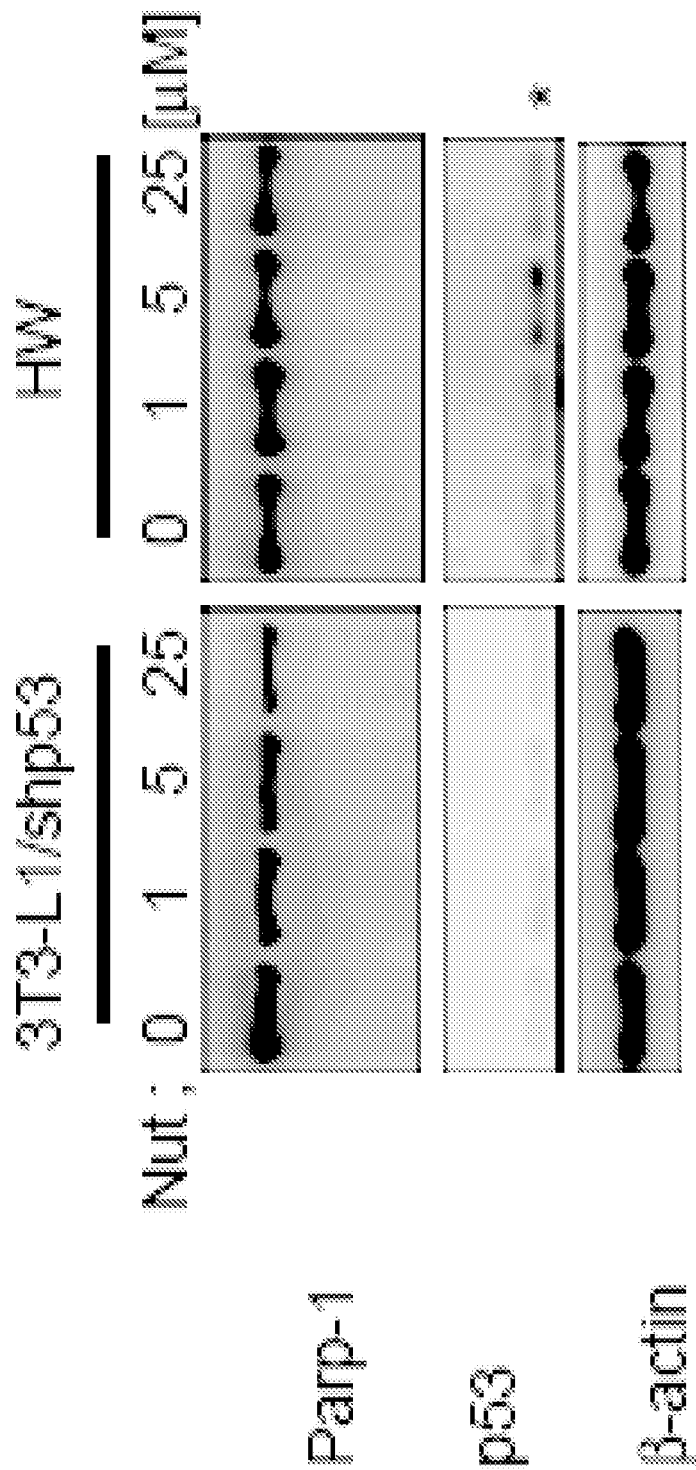

FIG. 2B shows HW, which is a mouse fibroblast cell line from p53 knockout mice, and 3T3-L1/shp53, which is a p53 stable knockdown cell line.

Figure 2C:
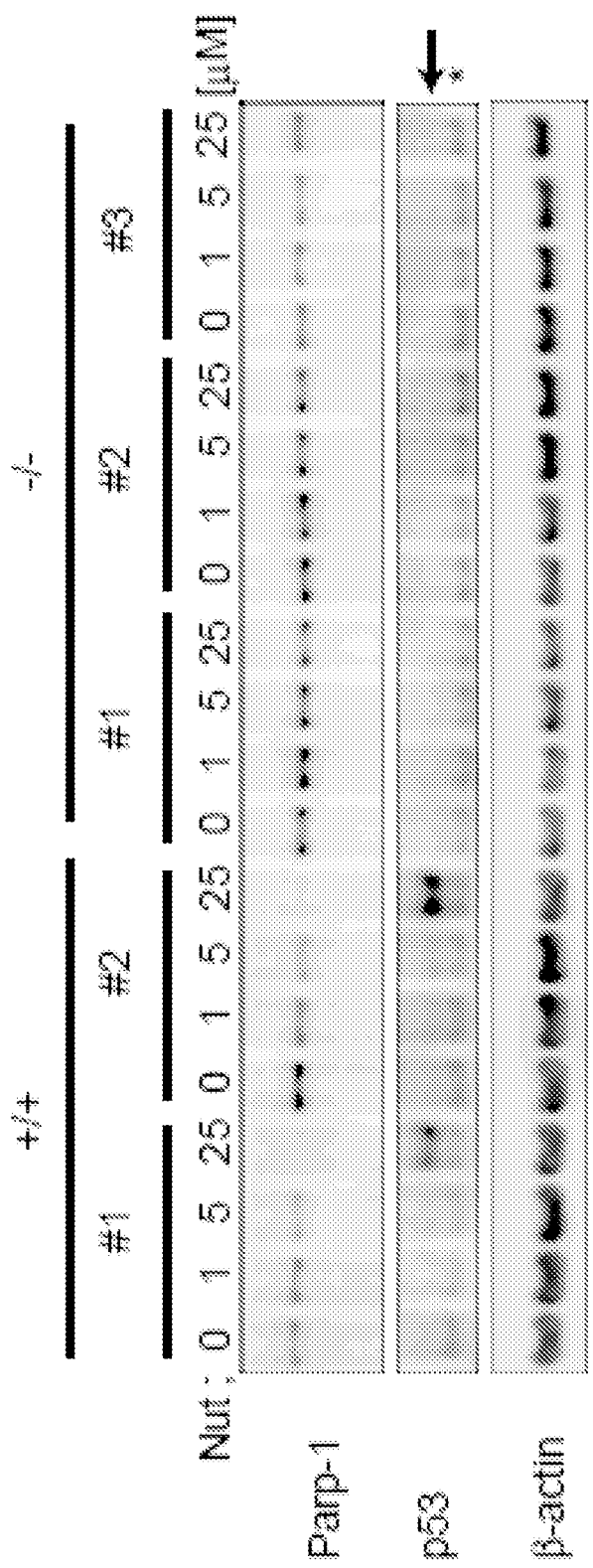

FIG. 2C shows that p53+/+ (n=2) and p53−/− (n=3) MEFs were treated with the indicated concentrations of Nutlin3a for 24 hours. The cell lysates were analyzed by Western blotting using the indicated antibodies. In the p53 panel, the arrow and asterisk respectively show the p53 and nonspecific bands.

All experiments were performed at least twice, and representative data are shown.

Figure 3A:
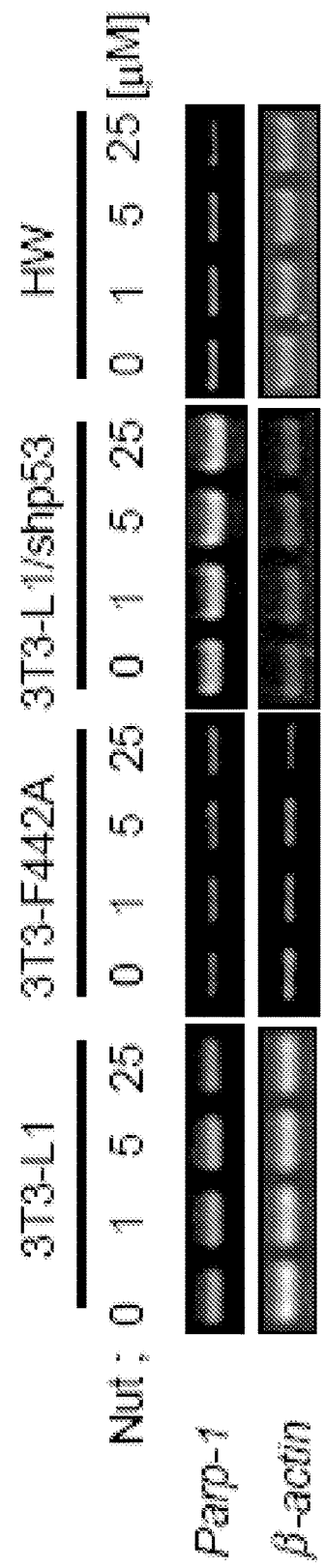

FIG. 3A shows that Nutlin3a downregulates Parp1 Protein Levels by Proteasomal Degradation. A, 3T3-L1, 3T3-F442A, 3T3-L1/shp53, and HW cells were treated with the indicated concentrations of Nutlin3a for 24 hours. Parp1 mRNA was detected by RT-PCR. β-actin was used as a loading control.

Figure 3B:
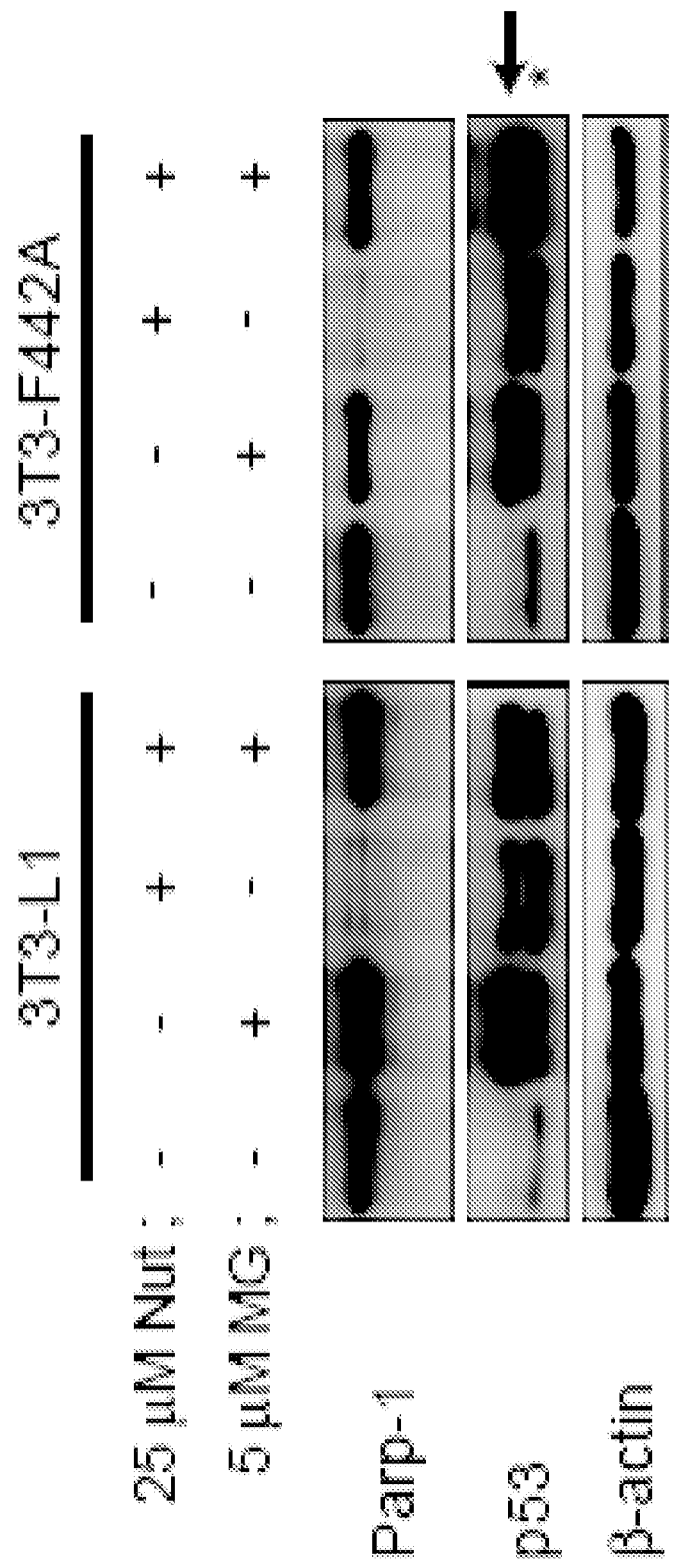

FIG. 3B shows that 3T3-L1 and 3T3-F442A cells were treated with 25 µM of Nutlin3a in the presence or absence of 5 µM of the proteasome inhibitor MG132 (MG) for 8 hours, and then the cell lysates were subjected to Western blotting using the indicated antibodies.

All experiments were performed at least three times, and representative data are shown.

FIG. 4A shows that Caylin2 induces decrease in Parp1 protein levels in mammalian cell lines but that Nutlin-3b does not. Mouse fibroblast 3T3-L1 (upper panel) or 3T3-F442A (lower panel) were treated with the indicated concentrations of Nutlin3a, Nutlin3b or Caylin2 for 8 hours. The cell lysates were analyzed by Western blotting using the indicated antibodies. In the p53 panel, the arrow and asterisk respectively show the p53 and nonspecific bands.

FIG. 4B is quantitative data from FIG. 4A.

Figure 4C:
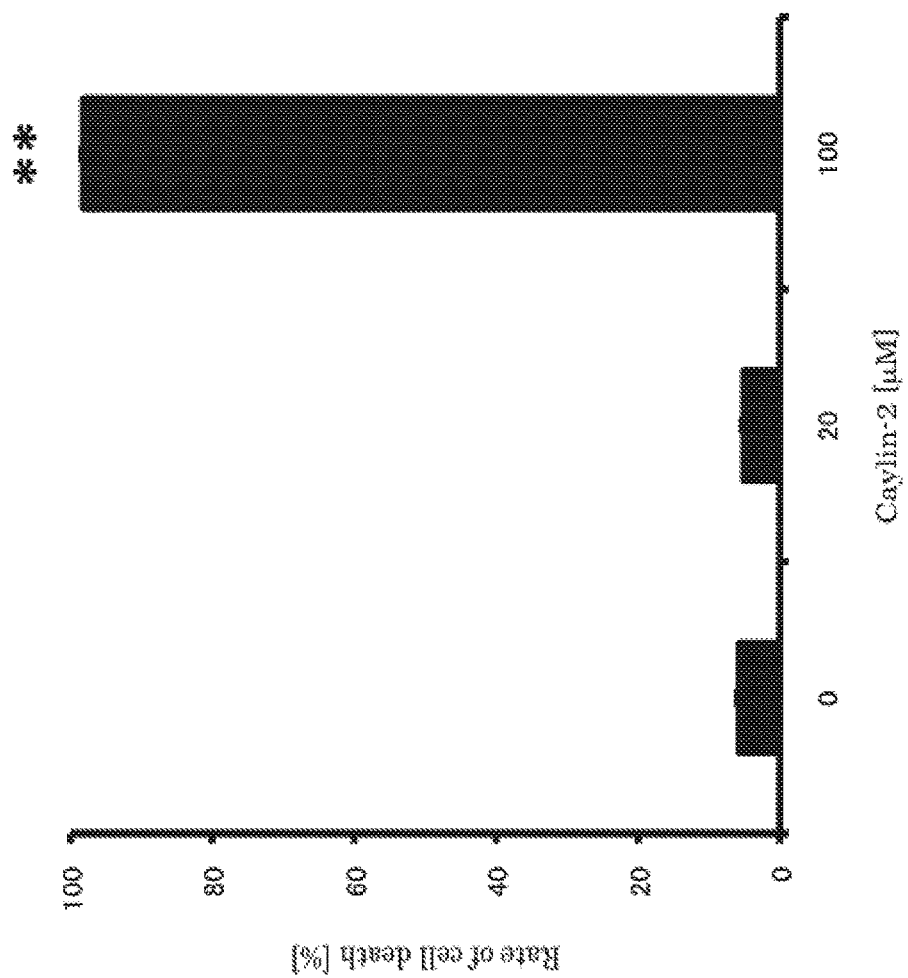

FIG. 4C shows that 3T3-L1 cells were treated with the indicated concentration of Caylin2 for 8 hours. The rate of cell death was analyzed by trypan blue staining.

All experiments were performed at least three times, and representative data are shown.

FIG. 5A shows that a decrease in Parp1 protein levels induced by Caylin2 is p53 status dependent. p53+/+ and p53−/− MEFs were treated with the indicated concentrations of Caylin2 for 8 hours. The cell lysates were analyzed by Western blotting using the indicated antibodies.

Figure 5B:
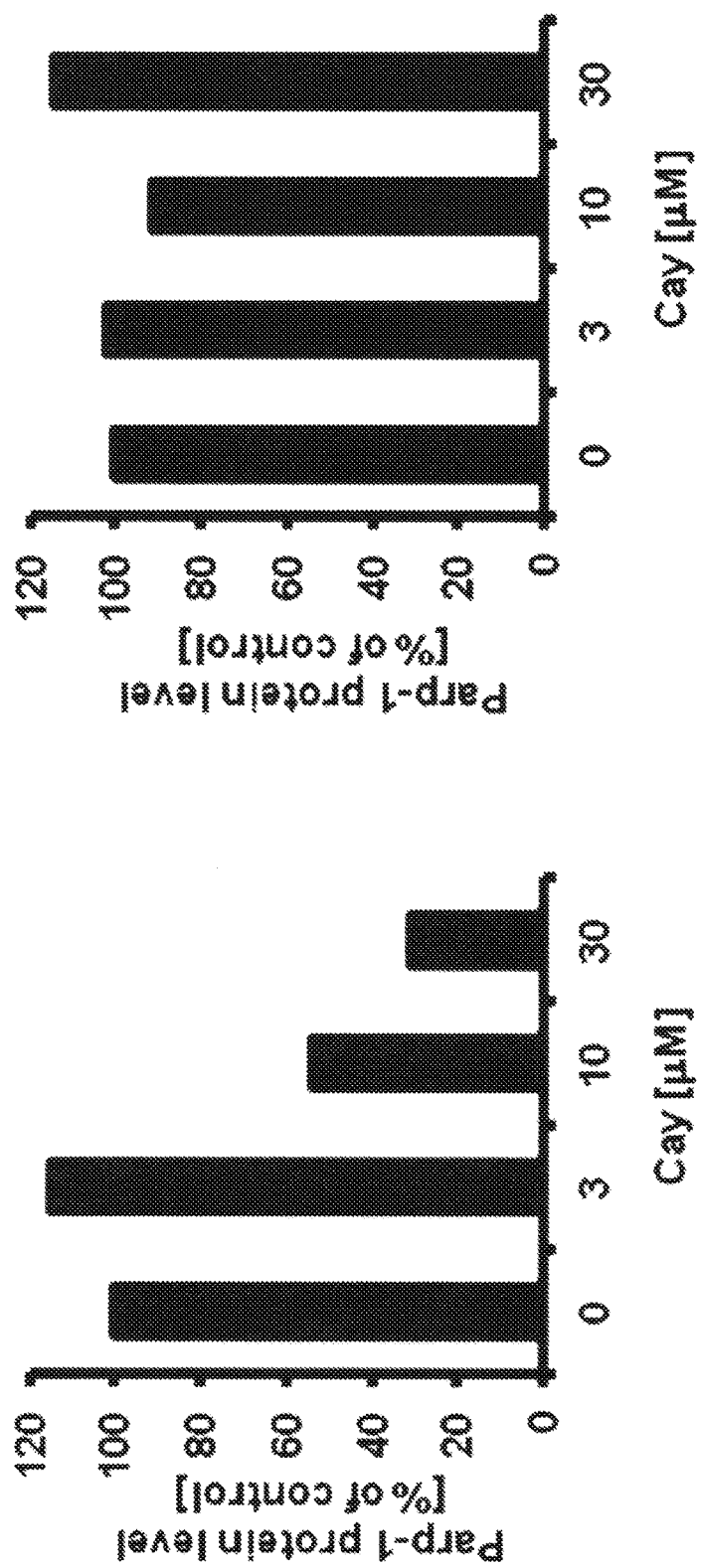

FIG. 5B is quantitative data from FIG. 5A. p53+/+ and p53−/−MEFs of every 2 to 3 clones were analyzed and representative data are shown.

FIG. 6A shows that 3T3-L1 cells were treated with 20 µM of Caylin2 for the indicated times. The proteins were subjected to Western blotting.

Figure 6B:
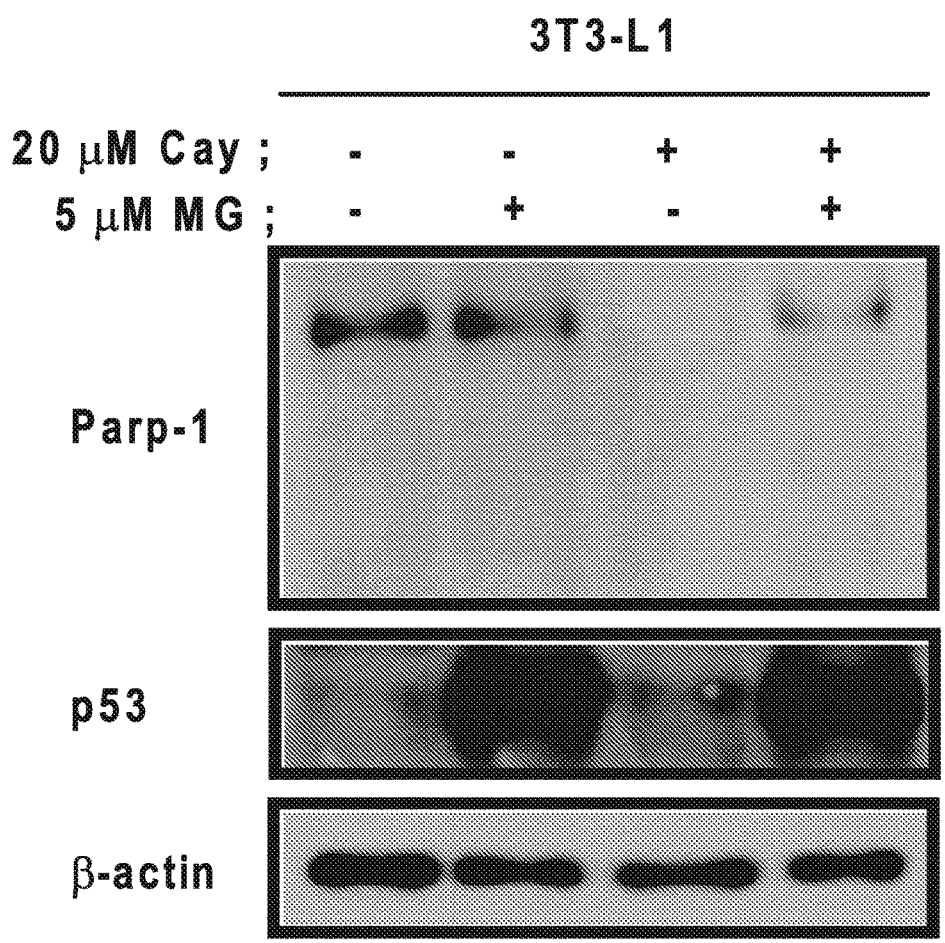

FIG. 6B shows 3T3-L1 cells were treated with 20 µM of Caylin2 in the presence or absence of 5 µM of the proteasome inhibitor MG132 (MG) for 8 hours, and then the cell lysates were subjected to Western blotting using the indicated antibodies.

DESCRIPTION OF EMBODIMENTS

The present invention provides an agent for treating ischemia/reperfusion injury, comprising administering to a mammal a therapeutically effective amount of a p53 agonist compound comprising a cis-imidazoline structure.

The present invention further provides a method of treating ischemia/reperfusion injury, comprising administering to a mammal a therapeutically effective amount of a p53 agonist compound comprising a cis-imidazoline structure.

The present invention provides a method of screening a therapeutic agent for treating an ischemia/reperfusion injury, comprising:

contacting a test substance with a p53-wild-type tester cell, of which an expression amount of Parp1 protein in a case in which the cell is contacted with Nutlin3a or Caylin2 is lower than that before contact with Nutlin3a or Caylin2, and thereafter measuring the expression amount of Parp1 protein in the tester cell to obtain a first measurement value;

contacting the tester cell with the test substance and a proteasome inhibitor, and thereafter measuring the expression amount of Parp1 protein in the tester cell to obtain a second measurement value; and selecting the test substance as a candidate substance for use as a therapeutic agent for treating an ischemia/reperfusion injury when the second measurement value is greater than the first measurement value.

Using Nutlin3a, we have analyzed p53 functions that are independent of DNA damage response and incidentally found that Parp1 proteins disappear in Nutlin3a-treated cells. In this study, we show the basic characterization of Nutlin3a-mediated Parp1 protein degradation and discuss the use of Nutlin3a as a Parp1 inhibitor for therapy and protection from ischemia/reperfusion injury.

Here we demonstrate that Nutlin3a treatment in mammalian cells reduces the protein levels of poly(ADP-ribose) polymerase) (Parp1). Parp1 functions in DNA repair, replication, and transcription and has been regarded as a target molecule for anti-cancer therapy and protection from ischemia/reperfusion injury. In this study, first we found that Nutlin3a, but not DNA damaging agents such as camptothecin (Cpt) and cisplatin, induced a decrease in the Parp1 protein levels. This decrease was not associated with cell death and not observed in p53 deficient cells. Next, because Nutlin3a treatment did not alter Parp1 mRNA levels, we expected that a protein degradation pathway might contribute to this phenomenon. Finally, we found that a proteasome inhibitor, MG132, inhibited the Nutlin3a-induced decrease in the levels of Parp1 protein. These results show that Nutlin3a induces the proteasomal degradation of Parp1 in a p53-dependent manner. Our findings will lead to the novel use of Nutlin3a as a Parp1 inhibitor for therapy and protection from ischemia/reperfusion injury.

The present invention is described in detail below. Although the below descriptions of the constituent elements sometimes refer to representative embodiments of the invention, the invention is by no means limited to the embodiments.

The term "ischemia/reperfusion injury" as used in the invention refers to disorders caused by an increase in the activity of Parp1 protein. Specific examples of the disorders include ischemic infarction such as cerebral infarction, myocardial infarction and pulmonary infarction, reperfusion disorders accompanying treatment of such infarctions, and tissue damage caused by vessel ligation and reperfusion during organ transplantation.

The term "a p53 agonist compound" as used in the invention refers to compounds that have a potent to induce p53 protein accumulation in vitro or in vivo. Specific examples of the p53 agonist compound comprising a cis-imidazoline structure include Nutlin3a, Caylin2, Caylin1 and pharmaceutically acceptable salts thereof.

In the invention, a p53 agonist compound comprising a cis-imidazoline structure is preferably selected from the group consisting of Nutlin3a, Caylin2, and pharmaceutically acceptable salts thereof.

In the invention, examples of the tester cell include a p53-wild-type cell of which the expression amount of Parp1 in a case in which the cell is contacted with Nutlin3a is lower than that before contact with Nutlin3a, and specific examples thereof include a p53-wild-type mouse fetus-derived fibroblast cell, mouse preadipocyte strains 3T3-L1 and 3T3-F442A and human lung carcinoma strain A549.

In the invention, examples of the proteasome inhibitor include MG132 (manufactured by Wako Pure Chemical Industries Ltd.), MG112, Lactacystin, Epoxomicin, PS-341 (Bortezomib), TMC-95A, Tyropeptin A, Salinosporamide A, Belactosin A, and Agosterol C.

In the invention, the term "contact" or "contacting" may refer to, for example, dissolving Nutlin3a, Caylin2 and/or another physiologically-active agent in a medium in which the tester cell is cultured, and culturing the tester cell for a certain period of time.

Examples

Examples of the invention are described below. However, the invention is not limited by the examples. In the descriptions below, "%" is based on mass unless indicated otherwise.

Experimental Procedures
Cell Culture and Drugs

Mouse fibroblast cell line 3T3-L1, human lung cancer cell line A549, and human hepatoma cell line HepG2 were purchased from the RIKEN Bioresource Center (Japan). Mouse fibroblast cell line 3T3-F442A and human osteosarcoma cell line U2OS were purchased from the European Collection of Animal Cell Cultures (U.K.). p53 deficient mouse-derived fibroblast cell line HW (J. Med. Chem. (2010) 53, 4561-4584) was kindly provided by Dr. Masayuki Saito (Tenshi University, Japan). The cells were maintained in Dulbecco's modified Eagle's medium (low glucose) (WAKO, Japan) with 10% (3T3-L1, 3T3-F442A, HW, U2OS, and HepG2) or 5% (A549) fetal calf serum and 1% penicillin/streptomycin (SIGMA). Cpt and MG132 were purchased from WAKO (Japan). Nutlin3a, Nutlin3b, and Caylin2 were supplied by Cayman (USA). p53 knockdown by shRNA We designed a mouse p53 shRNA expression vector based on target sequences for effective p53 knockdown, as previously reported (J. Biol. Chem. (2003) 278, 11731-11734). Two oligonucleotides, 5'-gatccccGTACGTGTG-TAGTAGCTTCttcaagagaGGAGCTATTACACATG-TACttttt ggaaa-3' (SEQ ID NO:1) and 5'-agcttttccaaaaaGTACATGTGTAATAGCTCCtctctt-gaaGAAGCTACTACACACGT ACggg-3' (SEQ ID NO:2) (upper case letters, target sequences against p53; lower case letters, BgIII, HindIII or loop structure sequences) were chemically synthesized (Operon Biotechnology, USA). The annealed oligos were directly ligated into a BgIII and HindIII-digested pSUPER-puro shRNA expression vector gifted from Dr. Shigeo Ohno (Yokohama City University, Japan) (Cell Sci. (2006) 119, 2107-2118). The produced vector, termed pSUPER-puro-shmp53, was transfected with Lipofectamine LTX (Invitrogen, USA) into 3T3-L1 cells, according to the manufacturer's protocol. For stable p53 knockdown cell lines, the transfected cells were selected with puromycin and resistant clones were isolated by trypsinization using cloning cylinders.

Preparation of Primary Mouse Embryonic Fibroblasts (MEFs)

p53 heterozygous mice (Accession Number, CDB 0001K) (Oncogene (1993) 8, 3313-3322) were purchased from RIKEN BRC (Saitama, Japan). p53 heterozygous males and females were crossed, and MEFs were prepared from the pregnant females. Each 13- to 15-day-old embryo was dissected from the uterus and washed with PBS. After removal of the head, tail, limbs, and blood-enriched organs, the trimmed embryo was washed with PBS and minced. After trypsinization at 37° C. for 10 min followed by inactivation of trypsin by addition of FCS, MEFs were separated by filtration through a cell-strainer. p53 status was confirmed by PCR using previously described primers (forward primer for p53 genomic sequence, 5'-AATT-GACAAGTTATGCATCCAACAGTACA-3' (SEQ ID NO:3); reverse primer for p53 genomic sequence, 5'-ACTC-CTCAACATCCTGGGGCAGCAACAGAT-3' (SEQ ID NO:4), forward primer for neo sequence, 5'-GAACCT-GCGTGCAATCCATCTTGTTCAATG-3' (SEQ ID NO:5)) (Oncogene (1993) 8, 3313-3322), and the established MEFs were maintained in DMEM high glucose with 10% FCS, 2-mercaptoethanol (2-ME), and antibiotics.

Western Blotting

Cells were lyzed by the addition of lysis buffer (50 mM Tris-HCl pH6.8, 2% SDS, 5% glycerol), boiled for 5 min, and sonicated. Protein concentrations of the soluble fraction were determined by BCA protein assay (PIERCE, USA) according to the manufacturer's protocol, and standardized by the addition of lysis buffer. Following this, the proteins were added to 2-ME and bromophenol blue so as to obtain final concentrations of 5% and 0.025%, respectively, and boiled for 5 min. Equal amounts of proteins (5 to 20 μg) were subjected to SDS-PAGE and transferred to nitrocellulose membranes. The membranes were blocked with 2.5% skim milk and 0.25% BSA in TBS (50 mM Tris, pH 7.4, 150 mM NaCl) containing 0.1% Tween 20 (TTBS) for 1 h at room temperature, and then probed with appropriate primary antibodies overnight at 4° C. or for 2 h at room temperature. As primary antibodies, anti-Parp1 (clone C-2-10, WAKO, Japan), anti-p53 (clone Ab-1, Calbiochem, USA), anti-βactin (clone AC-15, SIGMA, USA), or anti-caspase-3 (clone 1F3, MBL, Japan) antibodies were used. After washes with TTBS, the membranes were incubated with the appropriate secondary antibody, horseradish peroxidase-conjugated F(ab')2 fragment of goat anti-mouse IgG or anti-rabbit IgG (Jackson Immunoresearch, USA), for 1 h at room temperature. After washing the membrane with TTBS, the membranes were incubated with ImmunoStar LD reagent (WAKO, Japan). The specific proteins were visualized with LAS3000 (FUJI FILM, Japan), and the data were analyzed using MultiGauge software (FUJI FILM, Japan).

RNA Purification and RT-PCR

Cells were lyzed by RNAiso PLUS (TaKaRa, Japan), and then total RNA was purified using a FastPure RNA kit (TaKaRa, Japan) according to manufacturer's protocol. One mg RNA was subjected to reverse transcription with PrimeScript Reverse Transcriptase (TaKaRa, Japan) and random hexamer (TaKaRa, Japan). The PCR reaction was performed using Platinum Taq DNA Polymerase High Fidelity (Invitrogen, USA) and Parp1 (forward, 5'-TGCTCATCTTCAAC-CAGCAG-3' (SEQ ID NO:6); reverse, 5'-TCCTTTG-GAGTTACCCATTCC-3' (SEQ ID NO:7)) or β-actin primers (forward, 5'-TCTTTGCAGCTCCTTCGTTG-3' (SEQ ID NO:8); reverse, 5'-GGCCTCGTCACCCA-CATAG-3' (SEQ ID NO:9)) as follows: initiation step, at 94° C. for 1 min; amplification step, 30 (Parp1) or 25 (β-actin) cycles of at 94° C. for 1 min, at 52° C. (Parp1) or 61° C. (β-actin) for 15 sec, at 68° C. for 15 sec; termination step, 68° C. 15 sec. PCR products were subjected to 1.8% agarose gel electrophoresis, stained with ethidium bromide, and visualized with LAS3000. The data was analyzed using MultiGauge software (FUJI FILM, Japan).

Results

Nutlin3a Induces a Decrease in Parp1 Protein Levels in Mammalian Cell Lines.

When analyzing proteins of the Nutlin3a-treated mouse fibroblast cell line 3T3-L1, we observed a significant reduction in the levels of full length of Parp1 protein without cleavage into p85 and p25 apoptotic fragments. Interestingly, under this condition, a trypan blue exclusion assay showed that the cells were viable (data not shown), suggesting that the reduction of Parp1 protein was independent of cell death. To examine whether p53 stabilization induces the decrease in Parp1 protein, 3T3-L1 and 3T3-F442A mouse fibroblast cells were treated with a DNA damaging agent, Cpt, or Nutlin3a. As shown in FIGS. 1A and 1B, in both cell lines, Cpt treatment did not alter the Parp1 protein levels, and Nutlin3a markedly decreased it, although both drugs induced p53 stabilization. Furthermore, another DNA damaging agent, cisplatin, treatment and overexpression of p53 protein did not affect Parp1 protein levels (data not shown). Consistent with our previous observations, no caspase-3 activation, which is a hallmark of apoptosis, was detected in these conditions. The time course analysis showed that Parp1 protein diminished by a treatment with 25 µM Nutlin3a for 8 h (FIG. 1C). To confirm whether the Nutlin3a-induced Parp1 decrease is observed in human cells, we analyzed various Nutlin3a-treated human cell lines, A549, U2OS, and HepG2. As shown in FIG. 1D, we detected the Nutlin3a-induced Parp1 decrease in only A549 cells. These results suggest that in certain mammalian cells Nutlin3a induces the reduction of Parp1 protein in a cell death-independent manner.

Nutlin3a-Induced Decrease in Parp1 Protein is Mediated by p53.

Since Nutlin3a stabilizes p53 via inhibition of Mdm2, we examined whether p53 contributes to the Nutlin3a-induced Parp1 reduction. shRNA-mediated transient knockdown of p53 in 3T3-L1 cells attenuated the decrease in Parp1 by Nutlin3a treatment (FIG. 2A). Since p53 knockdown efficiency is not sufficient, we next analyzed this using two p53 deficient cell lines. 3T3-L1/shp53 cells were established by stable transfection with the pSUPER-puro-shmp53 plasmid vector followed by clone isolation, and its p53 protein expression levels were very much lower than in the transient knockdown. HW cells are a fibroblast cell line derived from p53 deficient mice. In these cell lines, the Nutlin3a-induced decrease in Parp1 was diminished significantly (FIG. 2B). Furthermore, we confirmed p53 dependency in the Nutlin3a-induced Parp1 reduction by using mouse embryonic fibroblasts derived from p53+/+ or −/− mice, and obtained similar results (FIG. 2C). These results show that Nutlin3a reduces the Parp1 protein levels in a p53-dependent manner.

Nutlin3a Down-Regulates Parp1 Protein Via Proteasome.

To examine whether the decrease in Parp1 protein by Nutlin3a treatment is caused by down-regulation of its mRNA, p53 proficient (3T3-L1 and 3T3-F442A) and deficient (3T3-L1/shp53 and HW) cell lines were treated with Nutlin3a, and then the Parp1 mRNA of each was analyzed by RT-PCR. Parp1 mRNA did not change in either p53 proficient or deficient cell lines, even at doses of Nutlin3a where levels of Parp1 protein were completely diminished (FIG. 3A). Therefore, we speculated that Nutlin3a-induced Parp1 reduction might involve proteasomal degradation. Thus, the effects of proteasome inhibition on Nutlin3a-induced Parp1 reduction were examined. Treatment with the proteasome inhibitor MG132 alone did not affect basal Parp1 protein levels, but it clearly inhibited the Nutlin3a-induced reduction in Parp1 (FIG. 3B). Taken together, these results indicate that the Nutlin3a treatment induced proteasome-mediated degradation of Parp1 protein.

Nutlin3b and Caylin2 were studied using the same method as in the case of Nutlin3a. The results are shown from FIG. 4A to FIG. 6B.

As shown in FIGS. 4A and 4B, in both cell lines, Nutlin3a and Caylin2, but not Nutlin3b, markedly decreased the Parp1 protein levels and induced p53 protein stabilization. These results suggest that in certain mammalian cells Caylin2 also induces the reduction of Parp1 protein in a cell death-independent manner. Interestingly, 100 µM Caylin2 treatment induced Parp1 cleavage, a hallmark of apoptosis, although 20 µM Caylin2 treatment induced Parp1 protein decrease without any trace of its apoptotic cleavage. This result also supports that the decrease in Parp1 protein level is not caused by cell death.

Furthermore, we confirmed p53 dependency in the Caylin2-induced Parp1 reduction by using mouse embryonic fibroblasts derived from p53+/+ or −/− mice, and obtained similar results to those of Nutlin3a treatment (FIGS. 5A and 5B). These results show that Caylin2 reduces the Parp1 protein levels in a p53-dependent manner.

Treatment with the proteasome inhibitor MG132 alone did not affect basal Parp1 protein levels, but it clearly inhibited the Caylin2-induced reduction in Parp1 (FIGS. 6A and 6B). These results indicate that the Caylin2 treatment induced proteasome-mediated degradation of Parp1 protein.

We demonstrated that the Mdm2 inhibitor, Nutlin3a and Caylin2, induce the reduction of Parp1 protein by a p53-dependent mechanism. Interestingly, DNA damaging agents (camptothecin and cisplatin), a proteasome inhibitor (MG132), and overexpression of p53 protein did not evoke a significant reduction in Parp1 protein, although these all induced p53 accumulation similar to Nutlin3a and Caylin2. These results suggest that in the process of Nutlin3a or Caylin2-induced Parp1 reduction, Mdm2 inhibition is more important than p53 accumulation. Therefore, we examined whether the other commercially available Mdm2 inhibitors induced a reduction in Parp1 protein in 3T3-L1 and A549 cells (data not shown). However, we could not identify Mdm2 inhibitors that induce a reduction in Parp1 protein in both cells. To conclude this issue, additional experiments with Mdm2 knockdown studies would be required.

We also showed that MG132 blocks the decrease in Parp1 protein. It was reported that Parp1 can be ubiquitinated in vivo, although it is unclear whether the ubiquitination is involved in proteasomal degradation of Parp1 (J. Cell.

Biochem. (2008) 104, 318-328). Taken together with our findings, it is likely that the ubiquitin-proteasome pathway directly regulates the degradation of Parp1 protein.

In comparison to the many Parp1 inhibitors evaluated in ongoing clinical trials (J. Med. Chem. (2010) 53, 4561-4584), the regulatory mechanism of Parp1 protein that we discovered provides some advantages. The first advantage is the novel mechanism of action as an inhibitor of the Parp1 signaling pathway. Because most of the Parp1-inhibiting compounds previously identified block the catalyzing activity of the protein, the specificity of these drugs in the other Parp family proteins that possess the highly conserved catalytic domain is a big issue (J. Med. Chem. (2010) 53, 4561-4584). On the other hand, Nutlin3a and Caylin2 inhibit Parp1 signaling via induction of Parp1 protein degradation. Therefore, we expect that the inhibition specificity for Parp1 protein in the Parp family could be high. In any case, it is important to analyze the effects of Nutlin3a and Caylin2 treatment on the protein levels of the other Parp family proteins. The second advantage is its cell type selectivity. A subset of cell lines that were used in this study was responsive to Nutlin3a, with decreases observed in Parp1 protein (FIG. 1A and FIG. 1D). It has been reported that Nutlin3a induces cleavage of Parp1 into two apoptotic fragments in the human colon cancer cell line, HCT116, and the human myeloid leukemia cell line, ML-1 (Mol. Cancer Res. (2007) 5, 1133-1145, Cell Cycle (2009) 8, 1711-1719). In fact, we confirmed that there was no significant reduction in Parp1 protein other than apoptotic cleavage in HCT116 cells treated with various doses of Nutlin3a (data not shown). Taken together, we believe that Nutlin3a or Caylin2-induced Parp1 degradation has cell type selectivity. Furthermore, as its clinical application, considering co-treatment with DNA damaging agents, Nutlin3a and Caylin2 may reduce side effects caused by DNA damaging agents. It is well known that alkylating agents cause Parp1 over-activation, resulting in massive inflammation due to undesirable necrotic cell death caused by NAD+ and ATP depletion (Proc. Natl. Acad. Sci. U.S.A. (1999) 96, 13978-13982, Mol. Cell. Biol. (1999) 19, 5124-5133), and that Parp1 is required for NF-κB transactivation involved in inflammatory responses (Am. J. Pathol. (2008) 173, 2-13). Therefore, co-treatment with Nutlin3a or Caylin2 may also attenuate necrotic cell death and inflammation induced by Parp1 over-activation.

Thus, elucidation of the regulatory mechanism according to which a p53 agonist compound comprising a cis-imidazoline structure induces elimination of Parp1 protein is important for the optimization of compounds inducing this phenomenon, resulting in establishment of selective chemotherapeutic strategies against cancer and ischemia/reperfusion injury.

The present application claims the benefits of priority to U.S. application Ser. No. 61/437,692, filed Jan. 31, 2011. The contents of that application are incorporated herein by reference in their entirety. All publications, patent applications, and technical standards mentioned in this specification are herein incorporated by reference to the same extent as if each individual publication, patent application, or technical standard was specifically and individually indicated to be incorporated by reference.

The invention claimed is:

1. A method of screening a therapeutic agent for treating an ischemia/reperfusion injury, comprising:

contacting a test substance with a p53-wild-type tester cell, wherein the p53-wild-type tester cell expresses an amount of Parp1 protein when the cell is contacted with Caylin2 that is lower than the amount of Parp1 protein in the cell before contact with Caylin2, and measuring the expression of Parp1 protein in the tester cell to obtain a first measurement value;

contacting the tester cell with the test substance and a proteasome inhibitor, and measuring the expression of Parp1 protein in the tester cell to obtain a second measurement value; and selecting the test substance as a candidate substance for use as a therapeutic agent for treating an ischemia/reperfusion injury when the second measurement value is greater than the first measurement value, the test substance selected as a candidate substance activating a proteasome to degrade Parp1 protein when the test substance is contacted with the p53-wild-type tester cell.

2. The method of screening a therapeutic agent for treating an ischemia/reperfusion injury according to claim 1, wherein the tester cell is a p53-wild-type mouse fetus-derived fibroblast cell.

* * * * *